United States Patent
Legay et al.

(10) Patent No.: US 9,566,437 B2
(45) Date of Patent: Feb. 14, 2017

(54) ACTIVE IMPLANTABLE MEDICAL DEVICE FOR HEART FAILURE THERAPY WITH STOCHASTIC STIMULATION OF THE VAGUS NERVE

(71) Applicant: SORIN CRM S.A.S., Clamart (FR)

(72) Inventors: Thierry Legay, Fontenay les Briis (FR); Hervè Blumstein, Mèvoisins (FR)

(73) Assignee: SORIN CRM SAS, Clamart (FR)

( * ) Notice: Subject to any disclaimer, the term of this patent is extended or adjusted under 35 U.S.C. 154(b) by 198 days.

(21) Appl. No.: 14/301,107

(22) Filed: Jun. 10, 2014

(65) Prior Publication Data
US 2014/0364921 A1    Dec. 11, 2014

(30) Foreign Application Priority Data

Jun. 11, 2013  (FR) ...................... 13 55383

(51) Int. Cl.
*A61N 1/08* (2006.01)
*A61N 1/36* (2006.01)

(52) U.S. Cl.
CPC ....... *A61N 1/36139* (2013.01); *A61N 1/36053* (2013.01); *A61N 1/36114* (2013.01); *A61N 1/36135* (2013.01)

(58) Field of Classification Search
CPC ............ A61N 1/36128; A61N 1/36146; A61N 1/36167; A61N 1/36053; A61N 1/36114; A61N 1/36135; A61N 1/36139
USPC .............................. 607/9, 17, 25, 72, 73, 62
See application file for complete search history.

(56) References Cited

U.S. PATENT DOCUMENTS

| | | |
|---|---|---|
| 2007/0233194 A1 | 10/2007 | Craig |
| 2008/0065158 A1* | 3/2008 | Ben-Ezra ........... A61N 1/36071 607/2 |
| 2008/0140141 A1* | 6/2008 | Ben-David ........ A61N 1/36114 607/9 |
| 2009/0088817 A1 | 4/2009 | Starkebaum et al. |
| 2011/0118802 A1 | 5/2011 | Usui |
| 2013/0131746 A1 | 5/2013 | Simon et al. |

OTHER PUBLICATIONS

Preliminary Search Report for French Patent Application No. FR1355383, dated Nov. 27, 2013, 2 pages.

* cited by examiner

*Primary Examiner* — Christopher D Koharski
*Assistant Examiner* — Michael Carey
(74) *Attorney, Agent, or Firm* — Foley & Lardner LLP

(57) ABSTRACT

A method for heart treatment includes analyzing the cardiac rhythm. The method further includes utilizing a generator to produce discharges ($S_i$) of N pulses (I) of VNS stimulation in succession. The discharge may be synchronized to a detected R ventricular depolarization wave of each cardiac cycle. The method further includes controlling a stochastic modulation of the discharges control of the delivery of each VNS pulse of each discharge by selective inhibition or not of the generation of these VNS pulses. The number of pulses of each discharge thus randomly varies, and thus varies the VNS stimulation energy of this discharge, which is artificially induced, cycle-to-cycle variability in the RR interval. This stochastic therapy is applied if the spontaneous heart rate variability falls below a minimum level.

20 Claims, 3 Drawing Sheets

ACTIVE IMPLANTABLE MEDICAL DEVICE FOR HEART FAILURE THERAPY WITH STOCHASTIC STIMULATION OF THE VAGUS NERVE

CROSS-REFERENCE TO RELATED APPLICATION

This application claims the benefit of and priority to French Patent Application No. 1355383, filed Jun. 11, 2013. French Patent Application No. 1355383 is hereby incorporated by reference in its entirety.

BACKGROUND

The invention relates to "active implantable medical devices" as defined by Directive 90/385/EEC of 20 Jun. 1990 of the Council of the European Communities, specifically implants for delivering therapies of stimulation of the vagus nerve, called VNS (Vagus Nerve Stimulation). The invention relates to the use of such therapies in patients at risk of heart failure.

Stimulation of the vagus nerve affects the cardiovascular functions by reducing the heart rate and myocardial contractility with decreased duration of diastole, which can help reduce the progression of cardiac remodeling that may lead to heart failure. Such VNS devices may include a lead, an electrode implanted on the vagus nerve, and a generator supplying VNS pulses on this electrode via the lead.

When the vagus nerve is stimulated in synchrony with the heartbeat, the device may include one or more cardiac leads. The cardiac leads may include, for example, one or more endocardial leads or one or more leads implanted in the coronary network for the collection of cardiac depolarization waves (electrogram EGM). In some devices the cardiac leads are also able to deliver myocardial stimulation pulses (stimulation of ventricular and/or atrial cavities), in addition to the VNS stimulation separately applied on the vagus nerve.

Other methods for detecting the heart rate may include collection of an subcutaneous electrocardiogram (ECG) using an implantable device dedicated to the VNS stimulation alone, the device not including cardiac lead or another mechanism to deliver pulses to the myocardium.

The application of a VNS stimulation delivered, in a period close to synchronism with the R wave of the EGM or ECG (the R wave corresponding to the beginning of the ventricular depolarization), has the effect of inducing a change in the RR interval of the successive cardiac cycles. The RR interval increases with the energy of the stimulation delivered to the vagus nerve, as a high VNS stimulation energy on cardiac function has an inhibitory effect resulting in a rhythm slowdown (measured by RR interval). Conversely, a low VNS stimulation energy has a lesser impact on cardiac function, resulting in a rhythm much closer to the natural sinus rhythm observable in the absence of VNS stimulation.

The evolution of the spontaneous heart rate variability (VSS) is one indicator for assessing the clinical condition of a patient experiencing or at risk of heart failure. A decrease in the VSS indicates a worsening of the heart failure disease. Conversely, an increase in VSS reflects an improvement in the general condition of the patient.

US2007/0233194A1 discloses a VNS electrostimulation device with a pulse generator synchronized to the heart and/or respiratory rate of the patient. The description includes methods for analyzing various cardiac and physiological parameters including heart rate variability (HRV). The sequencing of VNS pulses, in particular the moment for the application of the first pulse of the burst, may be modulated by the generator, randomly or in a predetermined manner. US2009/0088817A1, US2011/0118802A1 and US2013/0131746A1 disclose other examples of VNS stimulators wherein certain characteristics of the stimulation may vary randomly or in a predetermined manner.

SUMMARY

One embodiment of the invention relates to applying a VNS stimulation to a patient experiencing heart failure by modulating, cycle-to-cycle, the stimulation energy to induce changes in the RR interval of one cycle to another. This modulation is controllably caused to occur even though the sinus rhythm would have been constant in the absence of VNS stimulation. This device thus controls neurologically induced heart rate variability (hereinafter VSNI). In some embodiments, the modulation is only applied until the heart shows it has restored an increased spontaneous heart rate variability, indicating an improvement in the pathology of heart failure. The VSNI is then interrupted, but may continue later if the VSS decreases cross a predefined threshold.

According to one feature of the invention, the VSNI is of a stochastic type, that is to say it is non-deterministic (e.g., random, pseudo-random, etc.). This advantageously helps avoid compensation of the excitation of the vagus nerve by a physiological loop involving the central nervous system, which would reduce the beneficial effect resulting from VSNI. This stochastic modulation may be achieved by controlling, for each cardiac cycle, the delivery of VNS pulse discharges by a random or pseudo-random "heads or tails" type-function applied to the delivery of each pulse of each discharge. The VNS energy delivered on the nerve at each cardiac cycle thus varies between zero (no pulse delivered) and a maximum (all pulses of the discharge initially planned are delivered). Therefore, in each cardiac cycle a different, not predictable, energy is applied to the vagus nerve. This may causes a modulation of the RR interval in a predefined range between a zero value (no alteration of the RR interval) and a maximum value. The maximum value may be selected so that the VSNI does not exceed a value which would produce deleterious (e.g., arrhythmogenic), effects to the patient.

Embodiments of the invention relate to an active implantable medical device for the treatment of heart failure with vagus nerve stimulation synchronous with the heart activity. The device may implement methods for analyzing the cardiac rhythm able to collect an intracardiac electrogram EGM signal. The device may be configured to detect a ventricular R-wave depolarization in each heart cycle. The device may include a generator adapted to generate discharges, each discharge including N VNS stimulation pulses generable in succession, with N≥0. The generator may be capable of initiating the production of each potential discharge in synchronization with an R-wave of the instant of delivery of the first VNS pulse of this discharge. The device further may be configured to conduct stochastic modulation of the discharges. To achieve this, the device may be configured to separately control the delivery of each of the potential N VNS pulses of each discharge based on the result of a randomization. The methods for analyzing heart rate may include estimating a parameter of spontaneous heart rate variability of the heart rate. The stochastic modulation of the discharges may be selectively activated in accordance with said spontaneous heart rate variability parameter.

In some embodiments, the delivery of each pulse is a possible delivery, controllable by selective inhibition or not, of the generation of each of said VNS pulses. The number of pulses delivered in a VNS discharge may thus randomly vary. And, consequently, the energy contained in the VNS stimulation discharge may also vary. This may induce cycle to cycle variability of the RR interval.

Embodiments may include analyzing the heart rate are also able to estimate a parameter of spontaneous heart rate sinus variability. The stochastic modulation of the discharges may be selectively activated depending on this spontaneous heart rate variability estimate. The analysis methods of the cardiac rhythm can compare the spontaneous heart rate variability parameter to a predetermined minimum threshold. The stochastic modulation of the discharges may be selectively activated when this parameter is less than a predetermined minimum threshold.

The spontaneous heart rate variability parameter of the cardiac rhythm may be a measure of the variability of the RR interval. In varying embodiments the spontaneous heart rate variability parameters may be found, for example, by a measurement of the group including: the standard deviation over a given recording period of the RR intervals; the standard deviation over a given recording period of the average of the RR intervals on temporal segments of predetermined duration; and the root mean square of the variations in duration between consecutive RR intervals.

In some embodiments, the respective amplitudes of the VNS pulses delivered by the generator are all equal. In the same or yet other embodiments, the width of the pulses can stay constant. In the same or yet further embodiments, the respective time intervals separating the instants of possible application of two successive VNS pulses likely to be delivered by the generator at each discharge may be constant. Their delivery (or not) is determined by the stochastic modulation. The number N of the VNS pulses delivered by the generator for each discharge may be between 1 and 5.

DETAILED DESCRIPTION

Devices according to varying embodiments of the invention may include a microprocessor provided with programmable circuits for shaping and delivering stimulation pulses to implanted electrodes. The methods of the invention may be implemented by software (e.g., appropriate computer code algorithms executed by the microprocessor, a microcontroller or a digital signal processor of the device). The various processing are diagrammed herein by a number of different functional blocks in the form of interconnected circuits. Other embodiments may differ. The devices may include computer code modules for execution, discrete hardware components, or a combination thereof.

Figure 1:
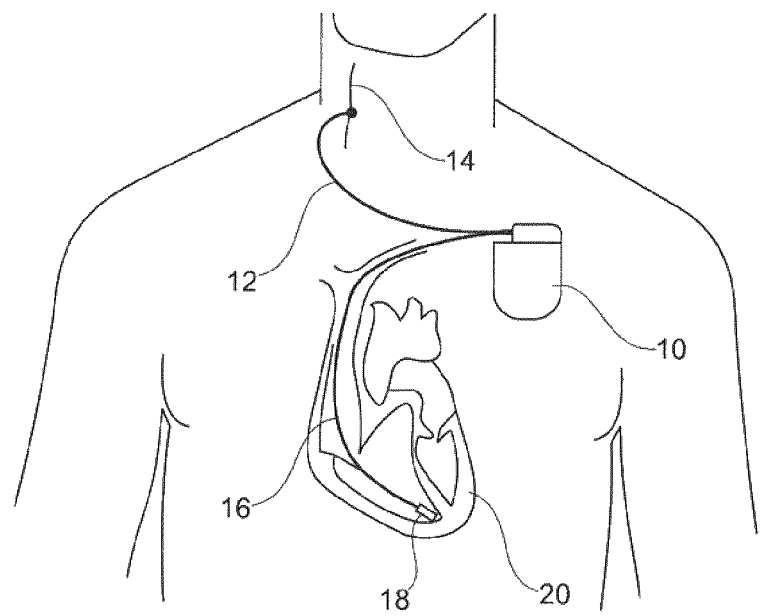
FIG. 1 is a presentation overview of the device of the invention, showing the generator, the myocardium and the vagus nerve, as well as the used leads.

In FIG. 1, a housing of a vagus nerve stimulation implantable generator 10 is shown. The stimulation is delivered by a lead 12. Lead 12 has, at its distal portion, an electrode implanted on the vagus nerve 14. The electrode delivers pulse discharges produced by the generator 10 to the vagus nerve 14.

The generator 10 may include a cardiac lead 16 having, at its distal end 18, an electrode for collecting the electrical activity of the myocardium 20. This lead collects endocardial electrogram EGM signals. The generator 10 may deliver pulses to the vagus nerve 14 at the same rate as heart beats and at the most appropriate moment of the cardiac depolarization wave. In other words, the cardiac leads and the overall logic of the device may be configured to allow delivery of VNS pulses in synchronism with the heartbeat.

Figure 2:
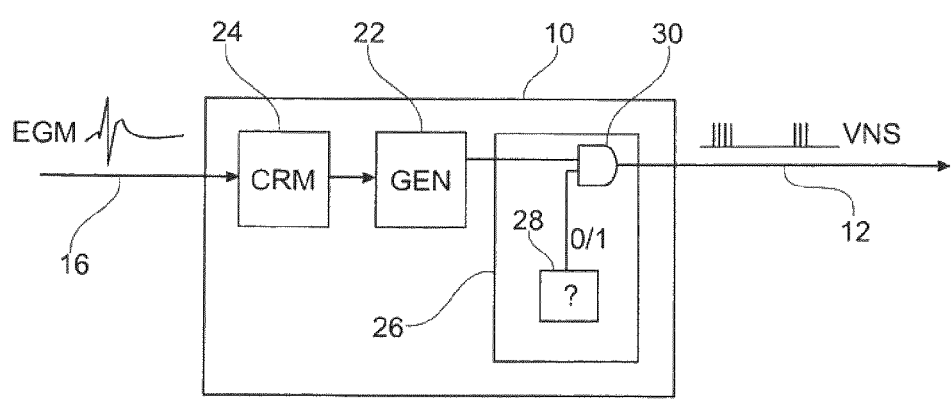
FIG. 2 is a block schematic view corresponding to the main features of the generator of the device of the invention.

FIG. 2 schematically illustrates the generator 10, according to an exemplary embodiment. The generator 10 includes a generator circuit 22 adapted to produce VNS pulse discharges delivered to the vagus nerve via the lead 12. The generator circuit 22 is controlled by a cardiac rhythm management (CRM) circuit 24. This control may be based on the EGM signal delivered by the lead 16.

Figure 3A:
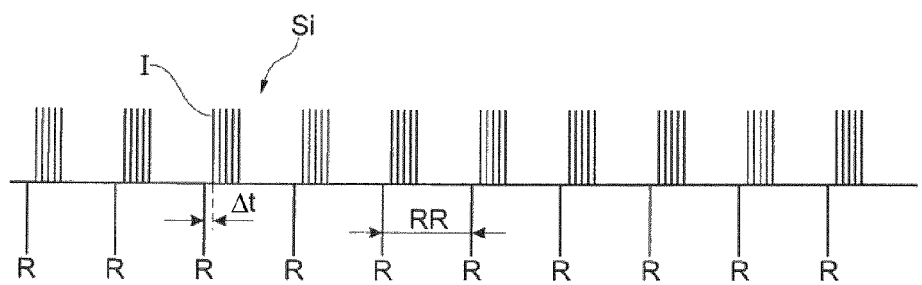
FIGS. 3a to 3c are figures for explaining the method of implementation of the invention, by timing diagrams showing different on a same temporal line a sequence of ten cardiac cycles, with the detected R waves and the applied VNS stimulation pulse discharges.

The CRM control circuit 24 can control the generator 22 to deliver VNS pulse discharges in synchronism with the heartbeat (judged by the R-wave markers, representative of the spontaneous depolarization peak of the ventricles). FIG. 3a illustrates the position of these markers R, whose rate, measured by the duration of successive RR intervals, is substantially regular. The discharges Si of VNS pulses are also shown on this timing diagram, these discharges being applied with or without delay after the R wave (in the example shown, they are applied with a delay $\Delta t$).

Each discharge Si of FIG. 3a is constituted by a plurality of individual pulses I, here five. The pulses are illustrated to have the same amplitude and the same width, so that all the pulses individually deliver the same VNS stimulation energy. Furthermore, also in this example, the interval between two successive pulses I of the same discharge is a constant interval.

The invention proposes to modulate the discharges successively applied to the vagus nerve in deciding at each discharge, to deliver a variable number of pulses. This technique is implemented by block 26 of FIG. 2. FIG. 2 schematically and symbolically shows the functions implemented by microprocessor-based control of the device. The blocks can correspond to computer code modules that, when executed by the microprocessor, carry out the activities and steps described herein.

The modulation circuit 26 is shown to include a binary pseudo-random generator 28 of the "heads or tails" type, thus providing at the output for each applied VNS pulse, a value of '0' or '1'V. These values may control the respective inhibition or authorization of the delivering of the VNS pulse, for each pulse I of each of the successive discharges Si (function schematized by the AND gate 30).

The "heads or tails" function can be obtained for example with an algorithm for pseudo-random selection of a number of N bytes, the "heads" being represented by the value '0' of a predetermined bit of this number and the "tails" by the value '1' of the same bit of the same number.

One can, for example, use an iterative algorithm defining a sequence S. For example, such that $S_{n+1}=(S_n*16807)$ modulo 4294967296, with $S_0$ arbitrarily chosen. $S_0$ may be, for example, a value representing the internal clock of a system or a combination of this internal clock and of another time-dependent parameter. The result '0' or '1' of the (n+1)th rank may be the value of one of any of the predetermined bits of $S_{n+1}$.

Figure 3B:
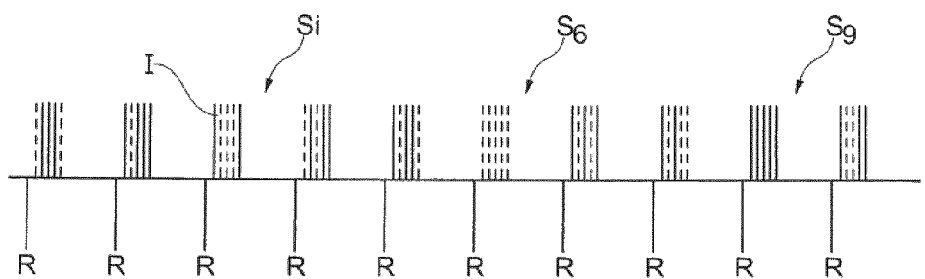

The result of a stochastic modulation function as may be provided by the device of FIG. 2, with inhibition/authorization of the issuance of each pulse of each discharge, is shown in FIG. 3b. FIG. 3b illustrates, with broken lines, discharges whose delivering was inhibited compared to FIG. 3a.

The energy delivered at each discharge (e.g., each discharge set) will thus vary, in an unpredictable manner, between a minimum and maximum:

The minimum corresponds to a situation wherein all of the discharge pulses have been inhibited, as in the case of the discharge $S_6$;

The maximum corresponds to the case wherein no pulses have been inhibited, as in the case of the discharge $S_9$.

The energy delivered to the vagus nerve thus varies randomly for each cycle, between zero and a maximum corresponding (in the example shown) to five times the energy of a unitary pulse I.

Figure 3C:
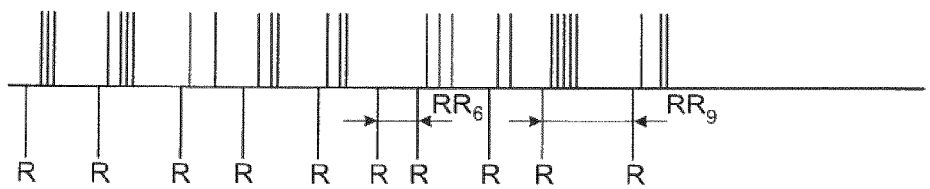

This modulation of the stimulation energy will cause a corresponding modulation of the RR interval, as shown in FIG. 3c, between:

A minimum value: in the illustrated example, the $RR_6$ interval corresponding to the minimum energy (actually zero) of the discharge $S_6$ wherein no pulse has been delivered; and A maximum duration, corresponding (in the illustrated example) to the $RR_9$ interval for the $S_9$ discharge.

As shown in FIG. 3c, a cycle to cycle high variability of the RR interval is thus induced.

The range of variation of this artificially induced RR interval may be selected, depending on the number of pulses of each individual discharge and of the energy of each pulse, so that this induced variability is tolerable by the patient and does not create a risk of deleterious effects, such as arrhythmogenic effect.

VNS stimulation as described above, with a cycle-to-cycle modulation to recreate a neurologically induced heart rate variability (VSNI), is applied only for a limited time, until it is determined the heart regained a sufficient spontaneous heart rate variability (VSS), revealing an improvement in the heart failure pathology. The VSNI is then stopped, and can be resumed later if it turns out that the VSS decreases to cross a predefined threshold.

Figure 4:
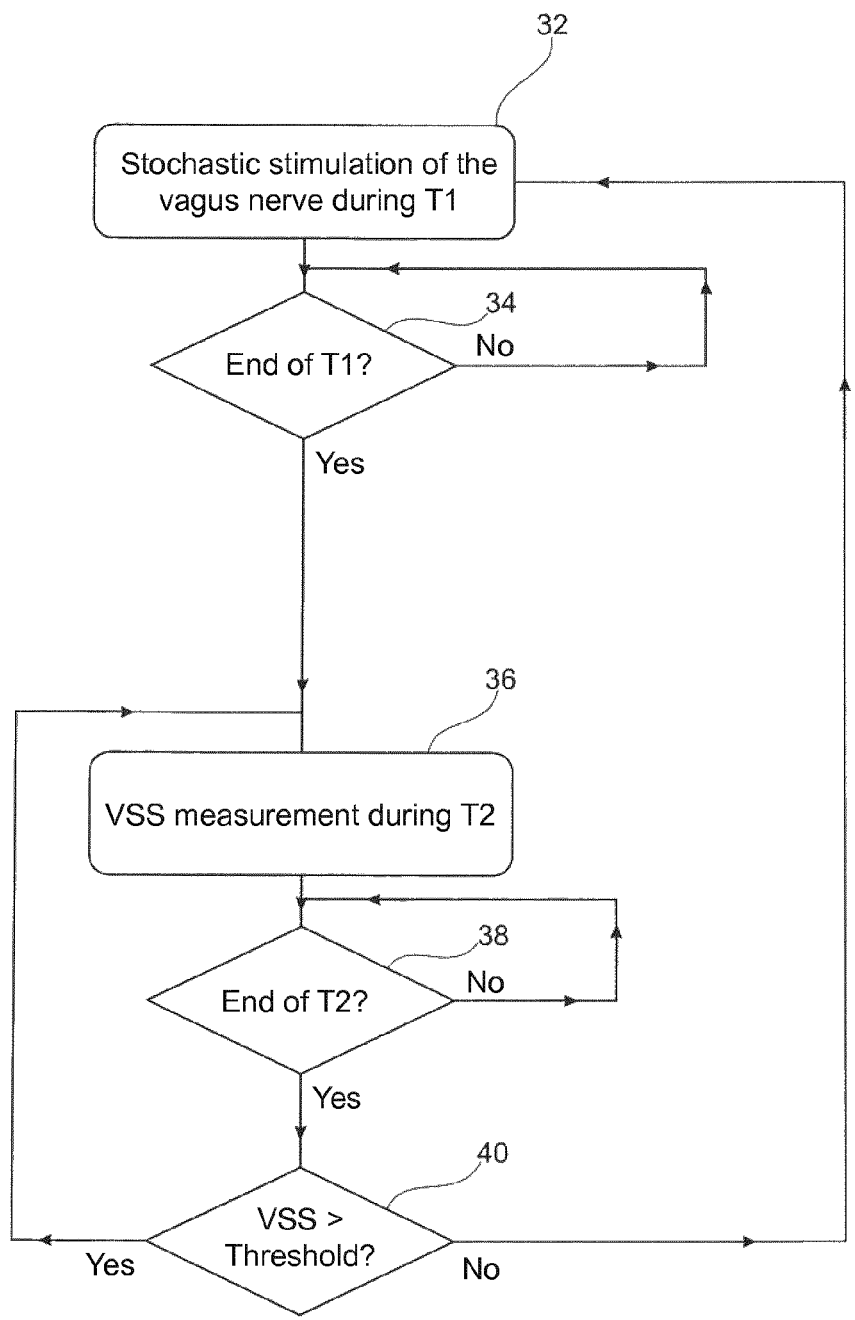
FIG. 4 is a flow-chart diagram summarizing the various stages of implementation of the technique of application of a VNS therapy according to the invention.

The sequence of these steps is illustrated in the flowchart of FIG. 4. VNS stimulation according to the invention is applied (block 32) for a predetermined time T1. Once this period has expired (test 34), the device evaluates the VSS during a period T2 corresponding to deactivation of the VNS stimulation and therefore the recovery of a natural rate (block 36).

One or more of a variety of methods can be used to measure the VSS spontaneous sinus rate variability such as the calculation of:

The standard deviation of RR interval over the entire recording period T2. This measure is an indicator of the overall variability;

The standard deviation of the average RR intervals on temporal segments of predetermined duration, e.g. five-minute segments, seen over the entire recording period T2. This measurement expresses the overall variability of the five minutes cycles, that is to say, a long-term variability; or Variations of the root mean square of duration between consecutive RR intervals (that is to say the square root of the average of squared differences, of durations between adjacent intervals). This measurement expresses in addition the high frequency variability, mainly from parasympathetic origin, modulated by respiration.

These various indices may be used to assess the cardiac response to stimulation of the autonomic nervous system. After a myocardial infarction, for example, the decrease of the spontaneous heart rate variability, expressed by such variables, is a predictive factor of mortality.

After expiry of the recording period T2 with disabling of VNS stimulation (test 38), the VSS variability measured during this period is compared to a predetermined threshold (test 40).

If the VSS variability remains below this threshold, then the VNS stimulation is resumed (back to block 32); otherwise, it means that the patient's condition has improved, and therefore the VNS stimulation remains deactivated and a new recording period T2 is initialized (back to block 36).

The invention claimed is:

1. An active implantable medical device for the treatment of heart failure with vagus nerve stimulation (VNS), synchronous with cardiac activity, including:
   a circuit configured to analyze the cardiac rhythm by collecting an intracardiac electrogram EGM signal and detecting a ventricular depolarization R-wave in each cardiac cycle;
   a generator, adapted to produce discharges, each discharge comprising N pulses of VNS stimulation generable in succession, with N≥0, the generator configured to initiate the production of each possible discharge VNS with an R-wave synchronization of the moment of delivery of the first VNS pulse of this discharge; and
   a lead coupled to the generator, wherein the lead is used by the generator to deliver each discharge and perform sensing,
   wherein the generator comprises a stochastic modulation module configured to separately controlling the delivery of each of the N possible VNS pulses of each discharge according to the result of a randomization;
   wherein the circuit for analyzing the cardiac rhythm is further configured to evaluate a spontaneous heart rate variability parameter (VSS) and wherein the stochastic modulation is activated in response to the spontaneous heart rate variability parameter falling below a threshold.

2. The device of claim 1, wherein the randomization varies the number of VNS pulses delivered in a discharge, varies the energy contained in VNS stimulation of this discharge, and wherein the randomization artificially induces a cycle-to-cycle variability of the RR interval.

3. The device of claim 1, wherein said parameter of spontaneous heart rate variability (VSS) of the heart rate is a measure of the variability of the RR interval.

4. The device of claim 3, wherein said measure of the variability of the RR interval is a measure of the group of: the standard deviation over a given recording period, of the RR intervals; the standard deviation over a given recording period, of the average of the RR intervals on temporal segments of predetermined duration; and the root mean square of the variations in duration between consecutive RR intervals.

5. The device of claim 1, wherein the amplitudes of VNS pulses delivered by the generator are all equal.

6. The device of claim 1, wherein the widths of the VNS pulses delivered by the generator are all equal.

7. The device of claim 1, wherein the time intervals between the possible instants of application of two successive VNS pulses delivered by the generator at each discharge are all equal, whether delivery by the generator is inhibited or not by the stochastic modulation.

8. The device of claim 1, wherein the number N of pulses VNS delivered by the generator for each discharge is between 1 and 5.

9. A device for controlling heart health treatment, comprising:
   a vagus nerve stimulation (VNS) lead and electrode;
   a control device coupled to the VNS lead and electrode, wherein the control device stochastically modulates a series of pulses of one or more VNS discharge bursts, wherein the control device activates the stochastic modulation when the control device determines that a spontaneous heart rate variability is below a predetermined threshold, and wherein the control device delivers the series of pulses of the VNS discharge bursts via the VNS lead and electrode.

10. The device of claim 9, wherein the VNS discharge bursts are synchronized to a detected R ventricular polarization wave of the cardiac cycle.

11. The device of claim 9, wherein the VNS pulses of the VNS discharge burst are constant in amplitude, duration, and spacing between potential pulses, wherein the variability is provided by the stochastic modulation.

12. The device of claim 9, wherein control device stochastically modulates the VNS discharge burst by varying a number of pulses of each VNS discharge burst or an energy contained in the VNS pulses of the VNS discharge, and wherein the control device artificially induces a cycle-to-cycle variability in an RR interval.

13. The device of claim 9, where the spontaneous heart rate variability is a measure of the variability of an RR interval.

14. The device of claim 13, wherein the measure of the variability of the RR interval is a measure of at least one of a standard deviation over a given recording period of the RR intervals, a standard deviation over a given recording period of the average of the RR intervals on temporal segments of predetermined duration, or a root mean square of the variation in duration between consecutive RR intervals.

15. The device of claim 9, wherein the series of pulses of each VNS discharge burst includes 1 to 5 pulses.

16. The device of claim 9, wherein a time interval between instants of application of two successive VNS pulses delivered at each VNS discharge burst are all equal.

17. The device of claim 16, wherein the control device inhibits or causes delivery of a pulse by the stochastic modulation.

18. The device of claim 10, wherein the series of pulses of each VNS discharge burst are applied with a delay after the detected R ventricular polarization wave.

19. The device of claim 1, where the N possible VNS pulses of each discharge are applied with a delay after the detected ventricular depolarization R-wave.

20. The device of claim 1, wherein the stochastic modulation is applied during a predetermined time.

* * * * *